(12) United States Patent
Orszulak

(10) Patent No.: US 8,257,349 B2
(45) Date of Patent: Sep. 4, 2012

(54) ELECTROSURGICAL APPARATUS WITH PREDICTIVE RF SOURCE CONTROL

(75) Inventor: James H. Orszulak, Nederland, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 739 days.

(21) Appl. No.: 12/389,168

(22) Filed: Feb. 19, 2009

(65) Prior Publication Data
US 2009/0248003 A1 Oct. 1, 2009

Related U.S. Application Data

(60) Provisional application No. 61/040,222, filed on Mar. 28, 2008.

(51) Int. Cl.
*A61B 18/04* (2006.01)
(52) U.S. Cl. .......................................... 606/34
(58) Field of Classification Search .............. 606/32–52
See application file for complete search history.

(56) References Cited

U.S. PATENT DOCUMENTS

| | | | |
|---|---|---|---|
| 5,370,645 | A | 12/1994 | Klicek et al. |
| 5,558,671 | A * | 9/1996 | Yates .............................. 606/38 |
| 5,688,267 | A | 11/1997 | Panescu et al. |
| 5,702,386 | A | 12/1997 | Stern et al. |
| 5,735,846 | A | 4/1998 | Panescu et al. |
| 5,755,715 | A | 5/1998 | Stern et al. |
| 5,817,093 | A | 10/1998 | Williamson, IV et al. |
| 5,906,614 | A | 5/1999 | Stern et al. |
| 5,957,961 | A | 9/1999 | Maguire et al. |
| 6,022,346 | A | 2/2000 | Panescu et al. |
| 6,053,912 | A | 4/2000 | Panescu et al. |
| 6,056,745 | A | 5/2000 | Panescu et al. |
| 6,113,591 | A | 9/2000 | Whayne et al. |
| 6,123,702 | A | 9/2000 | Swanson et al. |
| 6,162,217 | A | 12/2000 | Kannenberg et al. |
| 6,183,468 | B1 | 2/2001 | Swanson et al. |
| 6,235,020 | B1 | 5/2001 | Cheng et al. |
| 6,245,061 | B1 | 6/2001 | Panescu et al. |
| 6,245,065 | B1 | 6/2001 | Panescu et al. |

(Continued)

FOREIGN PATENT DOCUMENTS

DE 179607 3/1905
(Continued)

OTHER PUBLICATIONS

International Search Report EP09004250 dated Aug. 2, 2010.
(Continued)

*Primary Examiner* — Manuel Mendez

(57) ABSTRACT

An electrosurgical generator is disclosed, which includes a closed loop control system having a sensor system configured to sense tissue and/or energy properties at a tissue site and to generate a sensor signal representative of the tissue and/or energy properties. The control system includes a controller configured to select an electrosurgical operational mode from a plurality of electrosurgical operational modes in response to the sensor signal. A radio frequency arbitrary source is also included which is configured to generate a radio frequency input signal corresponding to the selected electrosurgical operational mode and a radio frequency output stage configured to generate a treatment signal which corresponds to the electrosurgical operational mode. The system also includes a predictive signal processor configured to adjust the radio frequency output stage in response to the radio frequency input signal, such that the radio frequency output stage alters the treatment signal in real time based on the selected electrosurgical operational mode.

20 Claims, 3 Drawing Sheets

U.S. PATENT DOCUMENTS

| | | | |
|---|---|---|---|
| 6,267,760 | B1 | 7/2001 | Swanson |
| 6,270,497 | B1 | 8/2001 | Sekino |
| 6,293,943 | B1 | 9/2001 | Panescu et al. |
| 6,494,880 | B1 | 12/2002 | Swanson et al. |
| 6,506,189 | B1 | 1/2003 | Rittman, III et al. |
| 6,575,969 | B1 | 6/2003 | Rittman, III et al. |
| 6,652,513 | B2 | 11/2003 | Panescu et al. |
| 6,733,495 | B1 | 5/2004 | Bek et al. |
| 6,749,624 | B2 | 6/2004 | Knowlton |
| 6,786,905 | B2 | 9/2004 | Swanson et al. |
| 6,855,141 | B2 | 2/2005 | Lovewell |
| 6,939,346 | B2 | 9/2005 | Kannenberg et al. |
| 6,962,587 | B2 | 11/2005 | Johnson et al. |
| 7,282,049 | B2 | 10/2007 | Orszulak et al. |
| 8,012,150 | B2 * | 9/2011 | Wham et al. .................... 606/38 |
| 2003/0199863 | A1 | 10/2003 | Swanson et al. |
| 2007/0129716 | A1 | 6/2007 | Daw |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1151725 | 11/2001 |
| EP | 880220 | 6/2006 |
| EP | 1810632 | 7/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO2008053532 | 5/2008 |

OTHER PUBLICATIONS

U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

* cited by examiner

ELECTROSURGICAL APPARATUS WITH PREDICTIVE RF SOURCE CONTROL

CROSS-REFERENCE TO RELATED APPLICATIONS

This application claims the benefit of priority to U.S. Provisional Application Ser. No. 61/040,222 entitled "ELECTROSURGICAL APPARATUS WITH PREDICTIVE RF SOURCE CONTROL" filed Mar. 28, 2008 by James H. Orszulak, which is incorporated by reference herein.

BACKGROUND

1. Technical Field

The present disclosure relates to electrosurgical apparatuses, systems and methods. More particularly, the present disclosure is directed to predictive signal processing of electrosurgical generator control signals to alter operational treatment modes during a given RF activation period.

2. Background of Related Art

Energy-based tissue treatment is well known in the art. Various types of energy (e.g., electrical, ultrasonic, microwave, cryo, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually of elongated cylindrical geometry) are inserted into a living body. A typical form of such needle electrodes incorporates an insulated sheath from which an exposed (uninsulated) tip extends. When an RF energy is provided between the return electrode and the inserted ablation electrode, RF current flows from the needle electrode through the body. Typically, the current density is very high near the tip of the needle electrode, which tends to heat and destroy surrounding tissue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

Conventional electrosurgical generators operate in one operational mode (e.g., cutting, coagulation, spray, etc.) which is set prior to commencement of the procedure during a given activation period. If during treatment a need arises to switch from one mode to another, such as during a cutting procedure when a vessel is cut and begins to bleed, the first mode (e.g., cutting) is terminated manually and the second mode (e.g., coagulation) is switched on. There is a need for an electrosurgical generator which can automatically switch among a plurality of operational modes in real time in response to sensed tissue and/or energy feedback signals.

SUMMARY

According to one aspect of the present disclosure, an electrosurgical generator is disclosed which includes a closed loop control system having a sensor system configured to sense tissue and/or energy properties at a tissue site and to generate a sensor signal representative of the tissue and/or energy properties. The control system includes a controller configured to select an electrosurgical operational mode from a plurality of electrosurgical operational modes in response to the sensor signal. A radio frequency arbitrary source is also included which is configured to generate a radio frequency input signal corresponding to the selected electrosurgical operational mode and a radio frequency output stage configured to generate a treatment signal which corresponds to the selected electrosurgical operational mode. The system also includes a predictive signal processor configured to adjust the radio frequency output stage in response to the radio frequency input signal, such that the radio frequency output stage alters the treatment signal in real-time based on the selected electrosurgical operational mode.

According to another aspect of the present disclosure, an electrosurgical system is disclosed. The system includes an electrosurgical generator includes a closed loop control system having a sensor system configured to sense tissue and/or energy properties at a tissue site and to generate a sensor signal representative of the tissue and/or energy properties. The control system includes a controller configured to select an electrosurgical operational mode from a plurality of electrosurgical operational modes in response to the sensor signal. The control system also includes a radio frequency arbitrary source configured to generate a radio frequency input signal corresponding to the selected electrosurgical operational mode and a radio frequency output stage configured to generate a treatment signal which corresponds to the electrosurgical operational mode. The control system also includes a predictive signal processor configured to adjust the radio frequency output stage in response to the radio frequency input signal, such that the radio frequency output stage alters the treatment signal in real-time based on the selected electrosurgical operational mode. The system also includes an electrosurgical instrument having one or more electrodes configured for application of electrosurgical energy associated with at least one electrosurgical mode. Such modes may include a cutting mode, coagulation mode, ablation mode, vessel sealing mode and/or arbitrary mix mode.

A method for controlling an electrosurgical generator is also contemplated by the present disclosure. The method includes the steps of sensing a tissue and/or energy property at a tissue site and generating a sensor signal representative of the tissue and/or energy property and selecting an electrosurgical operational mode from a plurality of electrosurgical operational modes in response to the at least one sensor signal. The method also includes the steps of generating a radio frequency input signal, using a radio frequency arbitrary source, corresponding to the selected electrosurgical operational mode and a predictive signal processor configured to adjust a radio frequency output stage in response to the radio frequency input signal, such that the radio frequency output stage alters a treatment signal in real-time which corresponds to the electrosurgical operational mode.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for predictive RF source control in an electrosurgical generator. This allows for alteration of treatment energy, e.g., selection of different modes, during a given RF activation period. Existing surgical procedures require a manual assisted mode selection for the application with no automated means to alter the treatment mode or to select a different mode once the generator has been activated. A predictive RF output electrosurgical sources provides for an arbitrary RF energy source to alter treatment energy and modes within the activation period, on a cycle-by-cycle basis or any number of cycles, without manual mode switching of the RF generator source. RF energy is delivered to tissue in real time under closed loop algorithm control based on selected mode and is adjusted dynamically based on predictive RF signal control. Predictive RF control manipulates the RF output stage to adjust applied power, voltage and current amplitude levels, RF frequency, RF gain, as well as adjusts the controlled rate of an RF parameter per unit time, which is unique to the treatment mode required to achieve the desired clinical effect.

The generator according to the present disclosure can perform at least monopolar and bipolar electrosurgical procedures, ablation and including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, coagulating, fusion, lesioning, etc.) and procedures (e.g., monopolar, bipolar, vessel sealing, ablation and mix mode).

Figure 1A:
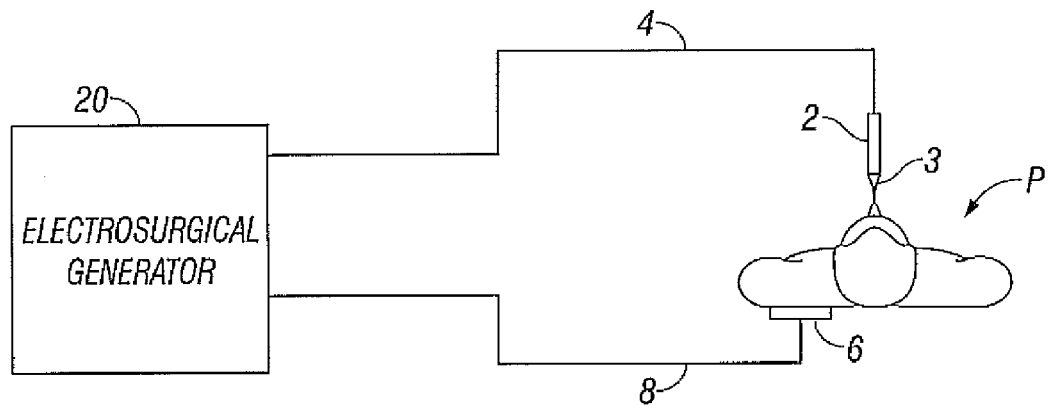
FIG. 1A is a schematic block diagram of a monopolar electrosurgical system according to the present disclosure.

FIG. 1A is a schematic illustration of a monopolar electrosurgical system according to one embodiment of the present disclosure. The system includes a monopolar electrosurgical instrument 2 including one or more active electrodes 3, which can be electrosurgical cutting probes, ablation electrode(s), etc. Electrosurgical RF energy is supplied to the instrument 2 by a generator 20 via an supply line 4, which is connected to an active terminal of the generator 20, allowing the instrument 2 to coagulate, ablate and/or otherwise treat tissue. The energy is returned to the generator 20 through a return electrode 6 via a return line 8 at a return terminal of the generator 20. The active terminal and the return terminal are connectors configured to interface with plugs (not explicitly shown) of the instrument 2 and the return electrode 6, which are disposed at the ends of the supply line 4 and the return line 8 respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Figure 1B:
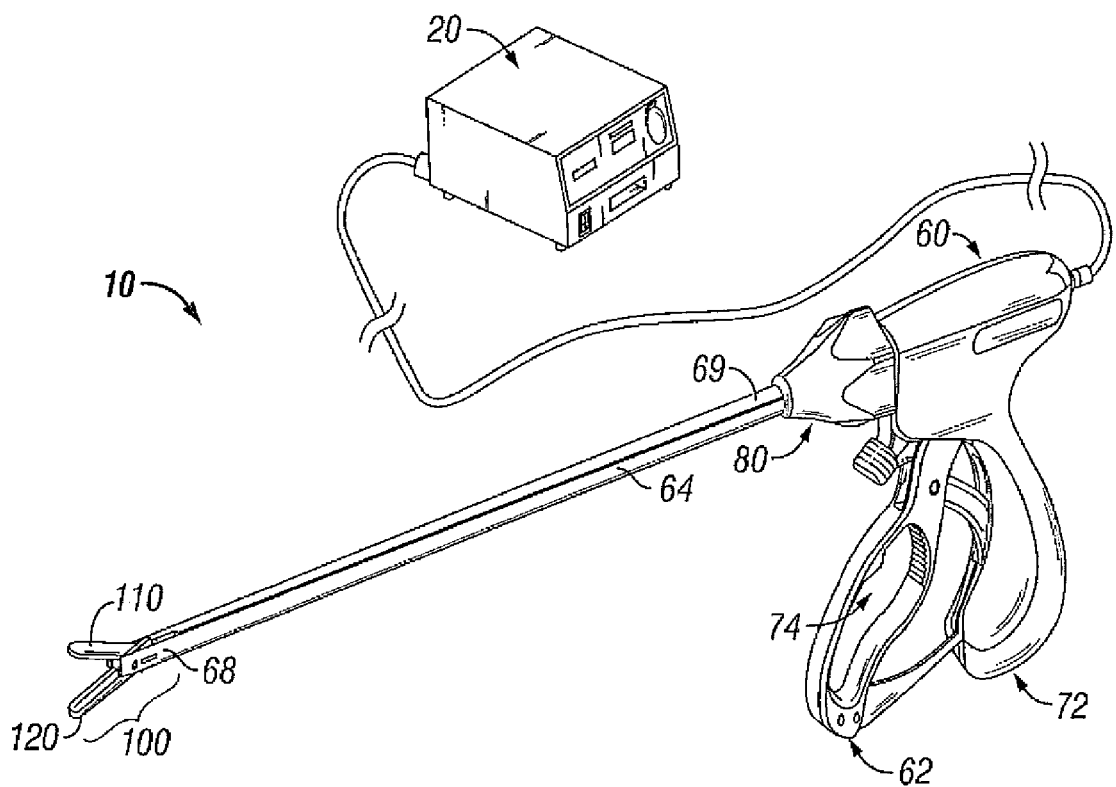
FIG. 1B is a schematic block diagram of a bipolar electrosurgical system according to the present disclosure.

The present disclosure may be adapted for use with either monopolar or bipolar electrosurgical systems. FIG. 1B shows a bipolar electrosurgical system according to the present disclosure which includes an electrosurgical forceps 10 having opposing jaw members 110 and 120. The forceps 10 includes one or more shaft members having an end effector assembly 100 disposed at the distal end. The end effector assembly 100 includes two jaw members movable from a first position wherein the jaw members are spaced relative to on another to a closed position wherein the jaw members 110 and 120 cooperate to grasp tissue therebetween. Each of the jaw members includes an electrically conductive sealing plate connected to the generator 20 which communicates electrosurgical energy through the tissue held therebetween.

Those skilled in the art will understand that the invention according to the present disclosure may be adapted for use with either an endoscopic instrument or an open instrument. More particularly, forceps 10 generally includes a housing 60, a handle assembly 62, which mutually cooperate with the end effector assembly 100 to grasp and treat tissue. The forceps 10 also includes a shaft 64 which has a distal end 68 which mechanically engages the end effector assembly 100 and a proximal end 69 which mechanically engages the housing 60 proximate the rotating assembly 80. Handle assembly 62 includes a fixed handle 72 and a movable handle 74. Handle 74 moves relative to the fixed handle 72 to actuate the end effector assembly 100 and enable a user to grasp and manipulate tissue. More particularly, the jaw members 110 and 120 move in response to movement of the handle 74 from an open position to a closed position. Further details relating to one envisioned endoscopic forceps is disclosed in commonly-owned U.S. application Ser. No. 10/474,169 entitled "Vessel sealer and divider" the entire contents of which is incorporated by reference herein.

Figure 2:
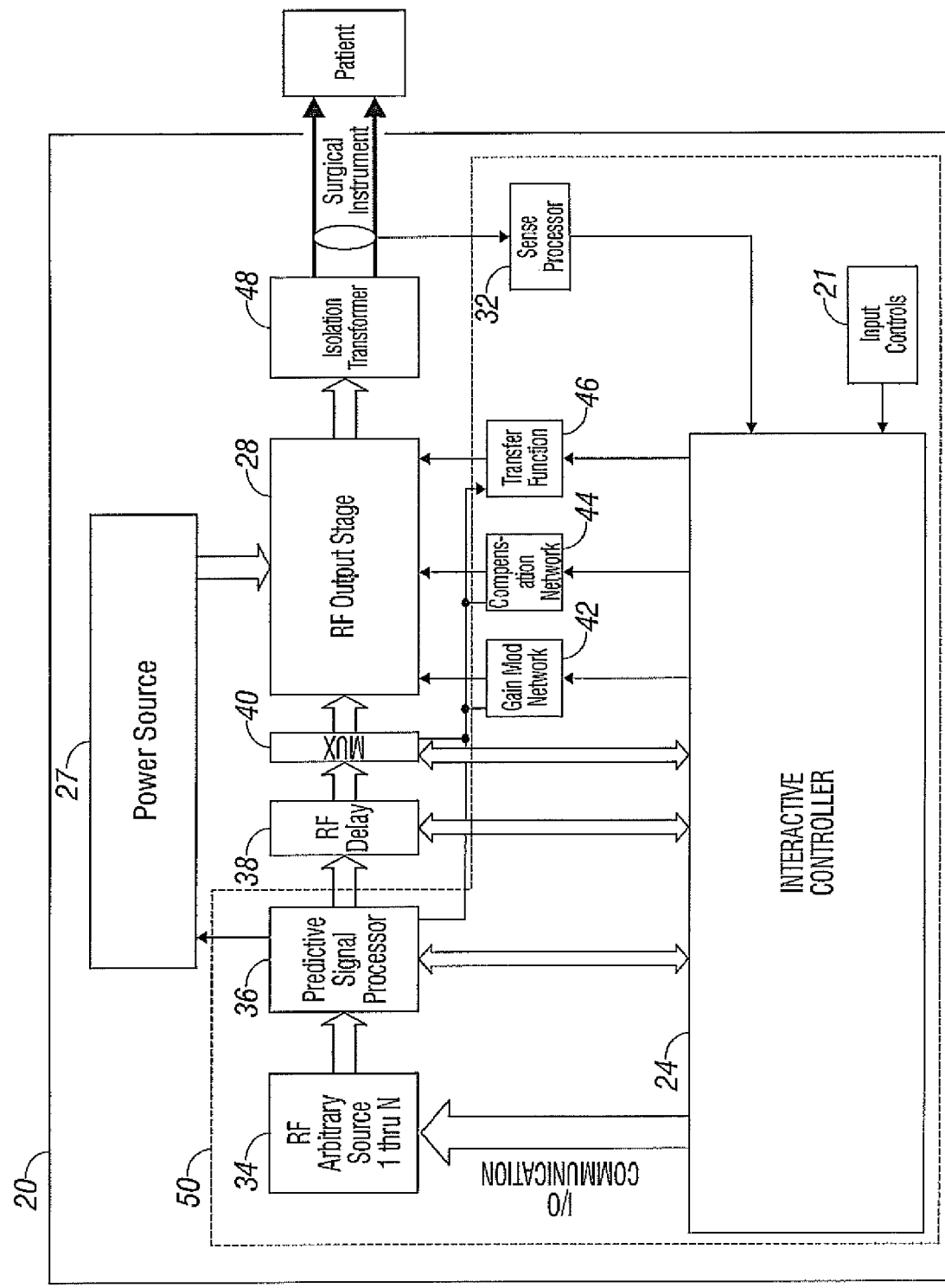
FIG. 2 is a schematic block diagram of a generator according to one embodiment of the present disclosure.

With reference to FIG. 2, a schematic block diagram of the generator 20 is shown. The generator 20 includes an interactive controller 24, a high voltage DC power source 27 ("HVPS") and an RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal. The energy is returned thereto via the return terminal. In particular, the RF output stage 28 generates a unique sinusoidal and or multi-configured arbitrary waveforms of high RF energy corresponding to the selected electrosurgical operational mode. The RF output stage 28 is configured to generate a plurality of treatment signals (e.g., waveforms) having a plurality of properties, such as frequency, duty cycle, amplitude (e.g., peak voltage and current), variety of waveshapes, controlled parametric rates per unit time, etc.

The generator 20 includes suitable input controls 21 (e.g., buttons, activators, switches, touch screen, etc.) for controlling the generator 20. In addition, the generator 20 may include one or more display screens for providing the user with variety of output information (e.g., intensity settings, treatment indicators, both in-process and endpoint, etc.). The controls 21 allow the user to select a desired operational electrosurgical mode as well as control other electrosurgical parameters to achieve the desired clinical result (e.g., coagulating, tissue sealing, tissue fusion, etc.). Each mode includes either a specific waveform, a sequenced set of waveforms, and/or arbitrary waveforms configured to effect the desired clinical result. Certain waveforms are suited for different surgical affects, e.g., cutting, coagulation, sealing, blend, etc. The "cutting" operational mode typically entails generating an uninterrupted sinusoidal waveform in the frequency range of 250 kHz to 4 MHz with a crest factor in the range of 1.4 to 2.0. The "blend" operational mode typically entails generating a bursted cut waveform with a duty cycle in the range of 25% to 75% and a crest factor in the range of 2.0 to 5.0. The "coagulate" operational mode typically entails generating a bursted waveform with a duty cycle of approximately 10% or less and a crest factor in the range of 5.0 to 12.0.

With continued reference to FIG. 2, the generator 20 includes a closed loop control system 50 for controlling energy output. The control system 50 includes a controller 24, a sense processor 32, a radio frequency arbitrary source 34 and a predictive signal processor ("PSP") 36 along with other components shown in FIG. 2 and discussed in more detail below. The closed loop control system 50 is a feedback control loop wherein the controller 24 signals any one or a plurality of the RF arbitrary source 34, the PSP 36, the HVPS 27, the RF output stage 28, the RF delay 38, the MUX 40, the Gain Mod network 42, the compensation network 44, and transfer function 46, to preset or dynamically adjust any one or a plurality of the above, to modify the delivered RF energy based on the sensed feedback signals.

The controller 24 includes a memory 26, which may be volatile type memory (e.g., RAM) and/or non-volatile type memory (e.g., flash media, disk media, etc.). Those skilled in the art will appreciate that the controller 24 may be substituted by any logic processor (e.g., control circuit) adapted to perform the calculations discussed herein. The controller 24 is coupled to the controls 21, arbitrary RF source 34, the PSP 36, RF delay network 38, multiplexer ("MUX") 40, gain modification network 42, compensation network 44 and transfer function network 46. Prior to commencement of treatment procedure, the user selects the desired electrosurgical operational mode via the controls 21, which transmit the selected mode to the controller 24. The controller 24 thereafter signals the arbitrary RF source 34 to generate a RF input signal representative of the selected electrosurgical operational mode.

The generated RF input signal is transmitted to the PSP 36 which processes the RF input signal using predictive signal recognition. PSP 36 evaluates the RF input signal and adjusts the treatment energy developed in and output by RF output stage 28. Depending on the structure of the RF input signal, PSP 36 may generate control signals for altering the operating characteristics of HVPS 27, and RF output stage 28. For example, PSP 36 control signals may be used to modify the HVPS 27 output voltage, RF output stage 28, gain mod network 42, compensation network 44, and transfer function 46. PSP 36 control signals may also be used to pre-set the initial operating characteristics of the HVPS 27 and RF output stage 28, and to communicate with interactive controller 24 in order to provide continual assessment of the RF input signal for dynamic adjustment of the RF output stage 28 during activation of the applied RF treatment energy.

Once treatment has commenced, the sense processor 32 continually senses tissue and/or energy properties. The sense processor 32 transmits sensor signals representative tissue and/or energy properties to the controller 24, which performs calculations to determine adjustments that may be made to the RF energy output. The sensor processor 32 may include a plurality of sensors measuring a variety of tissue and energy properties (e.g., tissue inpedance, tissue strain, tissue fusion, tissue hydration, tissue desiccation, tissue vascularity, tissue temperature, output current and/or voltage, etc.) and provides feedback to the controller 24. Such sensors are within the purview of those skilled in the art.

More specifically, the controller 24 sends and receives signals between the arbitrary RF source 34 and the PSP 36 to adjust the HVPS 27 and the RF output stage 28 based upon monitored tissue properties to achieve a desired clinical result. The arbitrary RF signal source is initially configured (e.g., via software) using instructions including appropriate energy content information corresponding to the selected electrosurgical treatment mode During operation, the electrosurgical mode is selected either manually (e.g., via controls 21) or automatically via the controller 24 based on the sensor signals received from the sense processor 32. In response to the selected mode, the arbitrary RF signal source 34 outputs the RF input signal which includes an amplitude, frequency and time variant parameters representative of the waveform associated with the selected electrosurgical operational mode.

The RF input signal is transmitted to the PSP 36 where the RF input signal is processed using predictive signal recognition to alter the operating characteristics of the RF output stage 28 and the HVPS 27. Namely, the RF input signal generated by the RF arbitrary source 34 is applied to the PSP 36 for analysis to generate control signal for modifying the HVPS 27 and/or the RF output stage 28. In particular, the PSP 36 determines operating parameters for the HVPS 27 and the RF output stage 28.

The PSP 36 and the controller 24 adjust the RF output stage 28 via the gain modification network 42, compensation network 44 and transfer function network 46. The networks 42, 44 and 46 are used to preset the RF output stage 28 prior to or during transmission of the RF input signal thereto. The networks 42, 44 and 46 modify the operating characteristics of the RF output stage 28 during switching between various electrosurgical operational modes. The gain modification network 42 presets the gain of the RF output stage 28 to adjust the RF output stage 28 during switching between low to high voltage electrosurgical operational modes. The compensation network 44 modifies parametric time rate of response of the RF output stage 28, to the RF input signal. The transfer function network 46 analyzes changes of the entire closed loop control system 50 and makes required adjustments. For example, the transfer function 46 may configure the RF output stage 28 for either voltage mode or current mode control of the applied RF input signal, for modifying the closed loop control system 50 as required to achieve the desired clinical effect.

Once the PSP 36 receives the RF input signal, the PSP 36 analyzes the detected peak signal amplitude thereof and utilizes the value to set the output voltage of the HVPS 27 as well as to adjust the operating power and/or voltage headroom of the RF output stage 28. Peak signal amplitude or RMS signal amplitude of the RF input signal may also be used to set the operating gain and transfer function of the RF output stage 28 through the networks 42, 44 and 46. The adjustments to the RF output stage may be done as a function of a ratio of output voltage or current to input voltage, a power gain output as a function of input voltage, or a parametric output function per unit of time.

The RF input signal passes through the RF delay 38 after being processed by the PSP 36 to allow the PSP 36 to adjust the RF output stage 28. Delaying the RF input signal allows the HVPS 27 to settle and prevents clipping of the RF output stage 28. The RF delay 38 provides a sufficient amount of time for the PSP 36 to preset the RF output stage 28 via the networks 42, 44 and 46. The delay is a predetermined time period such that dynamic changes in the amplitude of the RF input signal are tracked to modify the HVPS 27 as needed to conserve power. As the delay is executed, the PSP 36 and the controller 24 enable networks 42, 44 and 46 to select performance parameters of gain, compensation and transfer function setup.

Once the PSP 36 has adjusted the RF output stage to generate a desired waveform according to the selected mode, the RF input signal is transmitted to the MUX 40 which queues the RF input signals (if more than one signal is present) and passes the RF input signals to the RF output stage 28. The PSP 36 and the controller 24 may also provide control signal to MUX 40 for multiplexing RF input signals and/or operational mode sequencing to configure appropriate protocol for treatment delivery of the RF output stage 28. The RF output stage 28, upon completion of the performance parameter setup, generates output RF energy for treatment of tissue. The RF energy is delivered through an isolation transformer 48 to the tissue site, Within an activation period, as the tissue state changes with application of RF energy, the sense processor 32 reports monitored tissue and/or energy properties to the controller 24 for treatment protocol updates and/or adjustments. This may include the selection of a new, appropriate operational mode, to achieve the desired tissue clinical treatment effect. For example, a user may initially start the procedure by setting the generator 20 to a first mode (e.g., cutting). During the procedure, the sense processor 32 detects a change in tissue properties, such as a drop in tissue impedance attributable to a bleeding vessel. The change in impedance is transmitted to the controller 24, which determines that a change from the first mode to a second mode (e.g., coagulation, to seal the bleeding vessel) is required. The controller 24 signals RF arbitrary source 34, which alters the RF input signal to correspond with the newly selected mode. The PSP 36 receives the new RF input signals and adjusts the HVPS 27 and the RF output stage 28 to generate a waveform associated with the selected second mode. The adjustments to the RF output stage 28 may be made via the networks 42, 44 and 46 during predetermined delay, after which the RF output stage 28 generates a subsequent waveform corresponding to the second mode. Once the sense processor 32 determines that tissue and/or energy properties are within predetermined ranges a subsequent mode change may be requested back to the first mode or a third mode.

Figure 3:
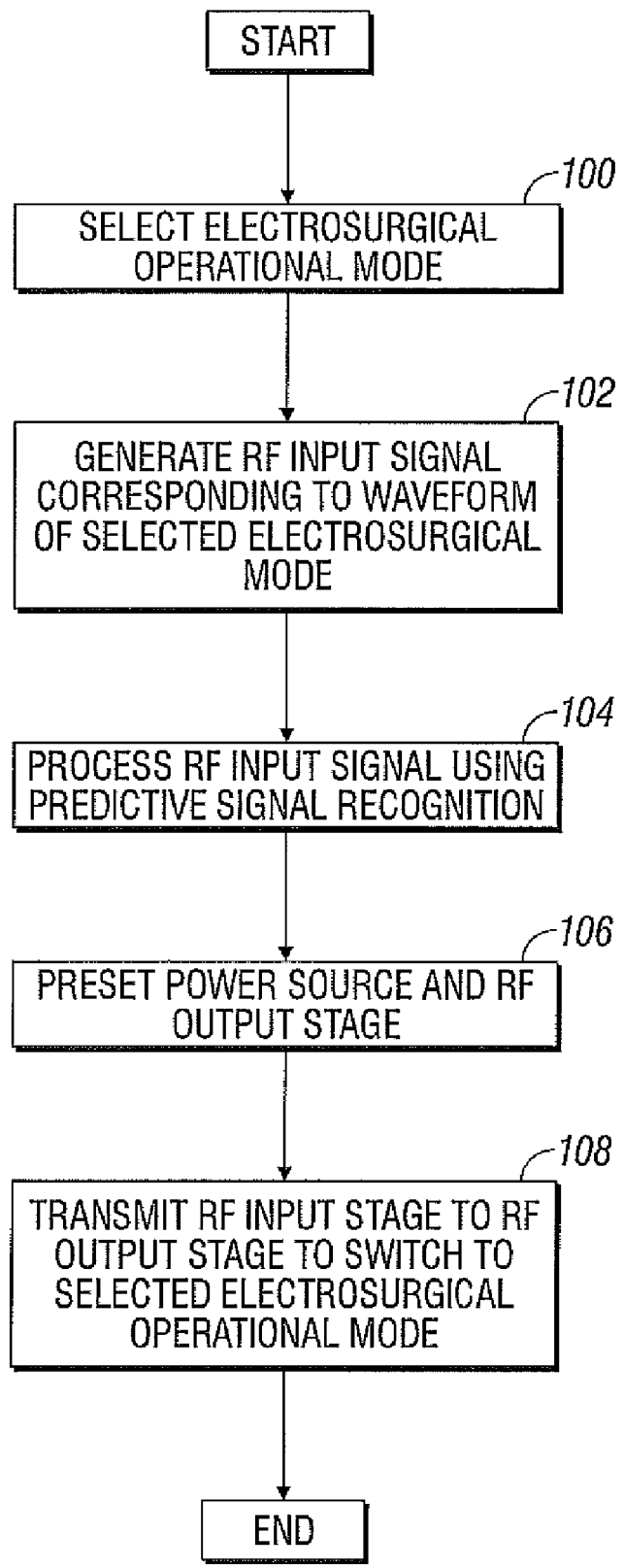
FIG. 3 is a flow diagram of a method according to one embodiment of the present disclosure.

FIG. 3 shows one method for predictive RF source control according to the present disclosure. In step 100 desired electrosurgical operational mode is selected (e.g., cutting). This is done either manually by the user via the controls 21 at the start or during the RF activation period or automatically during the RF activation period. Automatic selection of the mode is based on the sensor signals processed by the sense processor 32, which measures tissue and/or energy properties and provides the signals to the controller 24. Based on the sensor signals, the controller 24 determines whether the generator 20 should switch from a first mode to another mode, to alter the prescribed clinical treatment.

In step 102, the controller 24 signals the RF arbitrary source 34 to generate the RF input signal corresponding to the selected mode, specifically to the treatment signal (e.g., waveform) having a given waveshape or a sequence of waveforms having a multiple of dissimilar waveshapes. In step 104, the RF input signal is transmitted to the PSP 36 for predictive signal processing, which involves determining adjustments to the HVPS 27 and/or the RF output stage 28. In step 106, the HVPS 27 and the RF output stage 28 are preset. Initially, the RF input signal is delayed to allow for adjustments to the HVPS 27 and the RF output stage 28 to be made via networks 42, 44 and 46. In step 108, once the HVPS 27 and the RF output stage 28 are preset, the HVPS 27 generates sufficient voltage and the RF input signal is transmitted to the RF output stage 28 to generate a waveform corresponding to the selected electrosurgical treatment mode.

The generator according to present disclosure structures an arbitrary RF energy source to alter treatment energy during an activation period eliminating user directed manual mode selection. Unlike generators having resonant RF output stages which rely on calibrated open loop look up tables and/or outer loop control systems to compensate for tolerance variations in the delivered RF energy, a non-resonant approach with predictive RF processing of the present disclosure provides inner and outer loop control for greater precision in adjustment of the delivered RF energy. Decoding of the time variant parameter of the RF input signal is used to set appropriate compensation of the RF output stage and thus control the rate at which RF energy is applied. Power, voltage, current and tissue impedance rates of change etc. can now be more accurately controlled and applied per unit time. Detected fundamental RF operating frequency and its repetition rate can also be used to alter key RF output stage parameters to control depth of penetration of applied RF energy and minimize leakage of RF energy. Further, the predictive RF source generation system provides for adjustment of treatment energy parameters in real-time, such as power, voltage, current, frequency, gain, control rates and waveshape of the applied RF waveform.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator having a closed loop control system comprising:
   a sensor system configured to sense at least one of a tissue property and an energy property at a tissue site, and to generate at least one sensor signal representative of the at least one of the tissue property and the energy property;
   a controller configured to select an electrosurgical operational mode from a plurality of electrosurgical operational modes in response to the at least one sensor signal;
   a radio frequency (RF) arbitrary source configured to generate an RF input signal representative of the selected electrosurgical operational mode;
   an RF output stage configured to generate a treatment signal corresponding to the selected electrosurgical operational mode;
   a high voltage power source configured to generate sufficient voltage for the operation of the RF output stage; and
   a predictive signal processor configured to alter operating characteristics of the high voltage power source and the RF output stage in response to the RF input signal, such that the RF output stage alters the treatment signal in real time based on the selected electrosurgical operational mode.

2. An electrosurgical generator according to claim 1, wherein the predictive signal processor is configured to adjust the high voltage power source in response to the RF input signal.

3. An electrosurgical generator according to claim 1, wherein each of the plurality of the treatment signals includes a waveform configured for effecting a desired clinical result.

4. An electrosurgical generator according to claim 1, further comprising:
a gain modification network, a compensation network, and a transfer function network configured to preset or dynamically alter the RF output stage prior to or during transmission of the RF input signal thereto.

5. An electrosurgical generator according to claim 4, further comprising:
an RF delay network configured to delay transmission of the RF input signal to the RF output stage for a predetermined period of time until at least one of the gain modification network, the compensation network, and the transfer function network preset or dynamically alter the RF output stage.

6. An electrosurgical generator according to claim 1, wherein the RF input signal includes an amplitude.

7. An electrosurgical generator according to claim 6, wherein the predictive signal processor adjusts the RF output stage as a function of at least one of a peak signal and root mean square signal of the amplitude of the RF input signal.

8. An electrosurgical generator according to claim 1, wherein the RF input signal includes at least one of a frequency parameter and a time variant parameter.

9. An electrosurgical generator according to claim 1, wherein the controller is configured to select a sequence of electrosurgical operational modes from the plurality of electrosurgical operational modes in response to the at least one sensor signal.

10. An electrosurgical generator according to claim 1, wherein the plurality of electrosurgical operational modes comprises cut, coagulation, ablation, vessel sealing, arbitrary mix, and arbitrary waveform modes.

11. An electrosurgical generator according to claim 1, wherein the predictive signal processor is further configured to alter at least one operational characteristic of the electrosurgical mode so as to adjust at least one operating parameter of the RF output stage.

12. An electrosurgical generator according to claim 11, wherein the at least one operating parameter of the RF output stage may be adjusted on a cycle by cycle basis.

13. An electrosurgical generator according to claim 11, wherein the at least one operating parameter of the RF output stage may be adjusted as a variable integer number of RF cycles.

14. An electrosurgical generator according to claim 11, wherein the at least one operating parameter of the RF output stage includes at least one of power, voltage, current, frequency, gain, controlled parametric rates per unit time, and waveshape.

15. An electrosurgical system comprising:
an electrosurgical generator having a closed loop control system, the generator comprising:
a sensor configured to sense at least one of a tissue property and an energy property at a tissue site, and to generate at least one sensor signal representative of the at least one of the tissue property and the energy property;
a controller configured to select an electrosurgical operational mode in response to the at least one sensor signal;
a radio frequency (RF) arbitrary source configured to generate an RF input signal corresponding to the selected electrosurgical operational mode;
an RF output stage configured to generate a treatment signal which corresponds to electrosurgical operational mode;
a high voltage power source configured to generate sufficient voltage for the operation of the RF output stage; and
a predictive signal processor configured to alter operating characteristics of the high voltage power source and the RF output stage in response to the RF input signal, such that the RF output stage alters the treatment signal in real time based on the selected electrosurgical operational mode; and
an electrosurgical instrument having at least one electrode configured for application of electrosurgical energy associated with the electrosurgical operational mode.

16. An electrosurgical system according to claim 15, wherein the predictive signal processor is configured to adjust the high voltage power source in response to the RF input signal.

17. An electrosurgical system according to claim 15, the electrosurgical generator comprising:
a gain modification network, a compensation network, and a transfer function network configured to preset or dynamically alter the RF output stage prior to transmission of the RF input signal thereto.

18. An electrosurgical system according to claim 17, electrosurgical generator comprising:
an RF delay network configured to delay transmission of the RF input signal to the RF output stage for a predetermined period of time until at least one of the gain modification network, the compensation network, and the transfer function network preset or dynamically alter the RF output stage.

19. An electrosurgical system according to claim 15, wherein the RF input signal includes an amplitude.

20. An electrosurgical system according to claim 15, wherein the predictive signal processor adjusts the RF output stage as a function of at least one of a peak signal and root mean square signal of the amplitude of the RF input signal.

* * * * *